United States Patent
Antonucci et al.

(10) Patent No.: US 11,752,306 B2
(45) Date of Patent: Sep. 12, 2023

(54) LOW PROFILE PASSIVE PROTECTOR FOR AN I.V. CATHETER

(71) Applicant: Luther Needlesafe Products, LLC, Mission Viejo, CA (US)

(72) Inventors: Joseph G. Antonucci, Mission Viejo, CA (US); Joseph B. Antonucci, Mission Viejo, CA (US); Philip J. Antonucci, Mission Viejo, CA (US); John Muri, Mission Viejo, CA (US); Jeff Alan Burke, Murrieta, CA (US); Daniel Jason Velasco, Murrieta, CA (US); Joshua Alexander Sparks, Murrieta, CA (US); Kevin Martin Magrini, Murrieta, CA (US)

(73) Assignee: Luther Needlesafe Products, LLC, Mission Viejo, CA (US)

( * ) Notice: Subject to any disclaimer, the term of this patent is extended or adjusted under 35 U.S.C. 154(b) by 169 days.

(21) Appl. No.: 17/187,103

(22) Filed: Feb. 26, 2021

(65) Prior Publication Data

US 2022/0233824 A1 Jul. 28, 2022

Related U.S. Application Data

(60) Provisional application No. 63/140,357, filed on Jan. 22, 2021.

(51) Int. Cl.
*A61M 25/06* (2006.01)
*A61M 5/32* (2006.01)

(52) U.S. Cl.
CPC .... *A61M 25/0631* (2013.01); *A61M 25/0606* (2013.01); *A61M 25/0693* (2013.01);
(Continued)

(58) Field of Classification Search
CPC .......... A61M 25/0631; A61M 25/0606; A61M 25/0693; A61M 25/0625; A61M 5/3271;
(Continued)

(56) References Cited

U.S. PATENT DOCUMENTS

| 2,717,599 A | 9/1955 | Huber |
| 3,448,740 A | 6/1969 | Frank |

(Continued)

FOREIGN PATENT DOCUMENTS

| CN | 1046286 A | 10/1990 |
| CN | 1146918 A | 4/1997 |

(Continued)

OTHER PUBLICATIONS

Patent Cooperation Treaty, International Search Report and Written Opinion for International Application No. PCT/US 22/11317, dated Jul. 6, 2022, 9 pages.

*Primary Examiner* — Bhisma Mehta
*Assistant Examiner* — Robert F Allen
(74) *Attorney, Agent, or Firm* — STETINA BRUNDA GARRED AND BRUCKER

(57) ABSTRACT

A low-profile universal passive protector for an IV catheter includes a connector having a tubular body and a pair of arms pivotally connected thereto. The tubular body defines an end face and the connector includes a cavity extending from the end face. An elongate sheath is snap engageable to the tubular body. A spring is insertable within the connector cavity to extend between at least one of the pair of arms and the elongate sheath when received within the cavity. A slider is moveably coupled to the sheath. The slider includes a flashback chamber formed therein. A hypodermic needle is connected to the slider and is in fluid communication with the flashback chamber. The slider is moveable along the sheath between a first position and a second position, with (Continued)

the hypodermic needle being drawn into the sheath as the slider moves from the first position toward the second position.

20 Claims, 8 Drawing Sheets

(52) U.S. Cl.
CPC ....... *A61M 5/3271* (2013.01); *A61M 25/0625* (2013.01); *A61M 2005/3247* (2013.01); *A61M 2005/3249* (2013.01)

(58) Field of Classification Search
CPC .. A61M 2005/3247; A61M 2005/3249; A61M 25/0612; A61M 25/0618; A61M 25/0637; A61M 25/0643; A61M 25/06; A61M 25/065

See application file for complete search history.

(56) References Cited

U.S. PATENT DOCUMENTS

| | | | |
|---|---|---|---|
| 3,589,363 A | 6/1971 | Banko et al. |
| 3,612,050 A | 10/1971 | Sheridan |
| 3,645,268 A | 2/1972 | Capote |
| 3,780,733 A | 12/1973 | Martinez |
| 4,343,305 A | 8/1982 | Bron |
| 4,549,879 A | 10/1985 | Groshong et al. |
| 4,565,545 A | 1/1986 | Suzuki |
| 4,626,240 A | 12/1986 | Edelman et al. |
| 4,702,260 A | 10/1987 | Wang |
| 4,747,831 A | 5/1988 | Kulli |
| 4,762,516 A | 8/1988 | Luther et al. |
| 4,763,667 A | 8/1988 | Manzo |
| 4,767,407 A | 8/1988 | Foran |
| 4,781,691 A | 11/1988 | Gross |
| 4,790,828 A | 12/1988 | Dombrowski et al. |
| 4,795,446 A | 1/1989 | Fecht |
| 4,808,156 A | 2/1989 | Dean |
| 4,841,007 A | 6/1989 | Zdrahala et al. |
| 4,869,717 A | 9/1989 | Adair |
| 4,935,480 A | 6/1990 | Zdrahala et al. |
| 4,936,826 A | 6/1990 | Amarasinghe |
| 4,944,728 A | 7/1990 | Carrell et al. |
| 4,950,252 A | 8/1990 | Luther et al. |
| 4,964,854 A | 10/1990 | Luther |
| 4,978,344 A | 12/1990 | Dombrowski et al. |
| 4,994,041 A | 2/1991 | Dombrowski et al. |
| 5,106,376 A | 4/1992 | Mononen et al. |
| 5,135,502 A | 8/1992 | Koenig, Jr. et al. |
| 5,137,515 A | 8/1992 | Hogan |
| 5,215,525 A | 6/1993 | Sturman |
| 5,226,883 A | 7/1993 | Katsaros et al. |
| RE34,416 E | 10/1993 | Lemieux |
| 5,295,974 A | 3/1994 | O'Laughlin |
| 5,295,980 A | 3/1994 | Ersek |
| 5,300,045 A | 4/1994 | Plassche |
| 5,312,345 A | 5/1994 | Cole |
| 5,312,371 A | 5/1994 | Dombrowski et al. |
| 5,330,434 A | 7/1994 | Mcfarlane |
| 5,334,185 A | 8/1994 | Giesy et al. |
| 5,403,283 A | 4/1995 | Luther |
| 5,419,766 A | 5/1995 | Chang et al. |
| 5,531,701 A | 7/1996 | Luther |
| 5,533,988 A | 7/1996 | Dickerson et al. |
| 5,558,651 A | 9/1996 | Crawford et al. |
| 5,569,202 A | 10/1996 | Kovalic et al. |
| 5,569,217 A | 10/1996 | Luther |
| 5,575,777 A | 11/1996 | Cover et al. |
| 5,599,310 A | 2/1997 | Bogert |
| 5,611,781 A | 3/1997 | Sircom et al. |
| 5,634,913 A | 6/1997 | Stinger |
| 5,662,610 A | 9/1997 | Sircom |
| 5,683,370 A | 11/1997 | Luther et al. |
| 5,685,855 A | 11/1997 | Erskine |
| 5,688,249 A | 11/1997 | Chang et al. |
| 5,718,688 A | 2/1998 | Wozencroft |
| 5,830,190 A | 11/1998 | Howell |
| 5,865,806 A | 2/1999 | Howell |
| 5,891,098 A | 4/1999 | Huang |
| 5,913,848 A | 6/1999 | Luther et al. |
| 5,916,208 A | 6/1999 | Luther et al. |
| 5,935,108 A | 8/1999 | Katoh et al. |
| 5,957,893 A | 9/1999 | Luther et al. |
| 5,989,220 A | 11/1999 | Shaw et al. |
| 6,004,294 A | 12/1999 | Brimhall et al. |
| 6,056,718 A | 5/2000 | Funderburk et al. |
| 6,090,078 A | 7/2000 | Erskine |
| 6,203,533 B1 | 3/2001 | Ouchi |
| 6,213,978 B1 * | 4/2001 | Voyten ............... A61M 25/0631 604/164.01 |
| 6,217,527 B1 | 4/2001 | Selmon et al. |
| 6,379,333 B1 | 4/2002 | Brimhall et al. |
| 6,520,938 B1 | 2/2003 | Funderburk et al. |
| 6,595,954 B1 | 7/2003 | Luther et al. |
| 6,981,965 B2 | 1/2006 | Luther et al. |
| 7,753,887 B2 | 7/2010 | Botich et al. |
| 8,057,439 B2 | 11/2011 | Di Fiore |
| 2003/0083620 A1 * | 5/2003 | Luther ............... A61M 25/0606 604/164.07 |
| 2004/0167474 A1 | 8/2004 | Meng et al. |
| 2005/0015053 A1 * | 1/2005 | Parker ............... A61M 25/0631 604/164.12 |
| 2007/0088279 A1 | 4/2007 | Shue et al. |
| 2007/0161940 A1 | 7/2007 | Blanchard et al. |
| 2007/0191776 A1 | 8/2007 | Bialecki et al. |
| 2008/0287876 A1 | 11/2008 | Shue et al. |
| 2010/0056862 A1 | 3/2010 | Bakos |
| 2010/0081986 A1 | 4/2010 | Matson et al. |
| 2011/0001557 A1 | 1/2011 | Huang et al. |
| 2011/0015573 A1 | 1/2011 | Maan et al. |
| 2011/0168171 A1 | 7/2011 | Tsuboko et al. |
| 2012/0245562 A1 | 9/2012 | Bihlmaier |
| 2013/0053826 A1 | 2/2013 | Shevgoor |
| 2013/0060137 A1 | 3/2013 | Uber et al. |
| 2015/0025466 A1 * | 1/2015 | Antonucci ......... A61B 5/15003 604/164.08 |
| 2019/0184141 A1 | 6/2019 | Antonucci |

FOREIGN PATENT DOCUMENTS

| | | |
|---|---|---|
| CN | 1173376 A | 2/1998 |
| CN | 201101798 Y | 8/2008 |
| EP | 343803 A2 | 11/1989 |
| EP | 475375 A1 | 3/1992 |
| EP | 645159 A1 | 3/1995 |
| EP | 734739 A2 | 10/1996 |
| EP | 747083 A2 | 12/1996 |
| EP | 791370 A1 | 8/1997 |
| EP | 830872 A2 | 3/1998 |
| EP | 1110576 A1 | 6/2001 |
| JP | 08257129 A | 10/1996 |
| JP | 09099069 A | 4/1997 |
| JP | 2962268 B2 | 10/1999 |
| WO | 9553509 A1 | 12/1995 |
| WO | 9908742 A1 | 2/1999 |
| WO | 0006226 A1 | 2/2000 |
| WO | 0013728 A1 | 3/2000 |
| WO | 2004045701 A1 | 6/2004 |
| WO | 2007098355 A1 | 8/2007 |

* cited by examiner

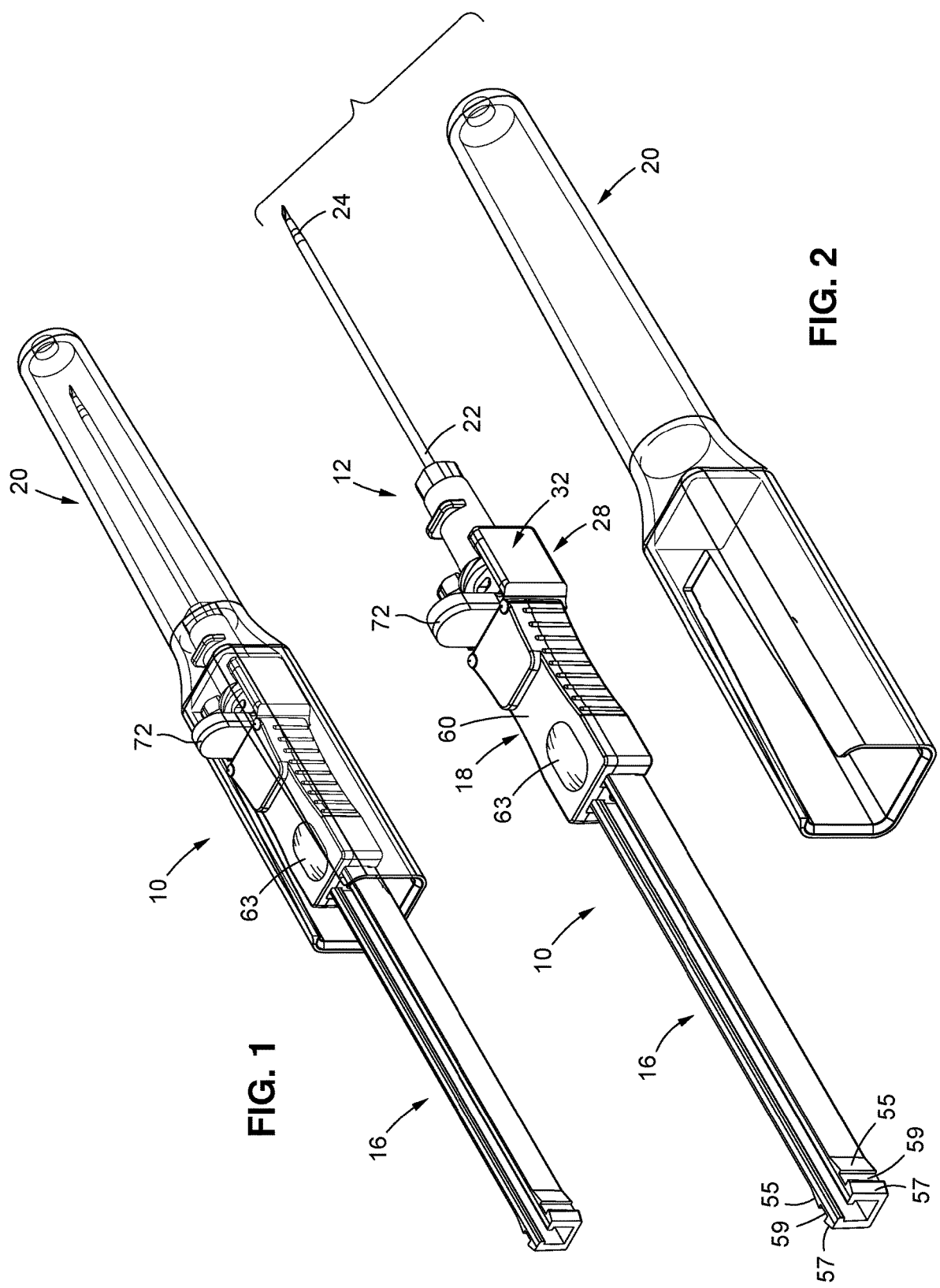

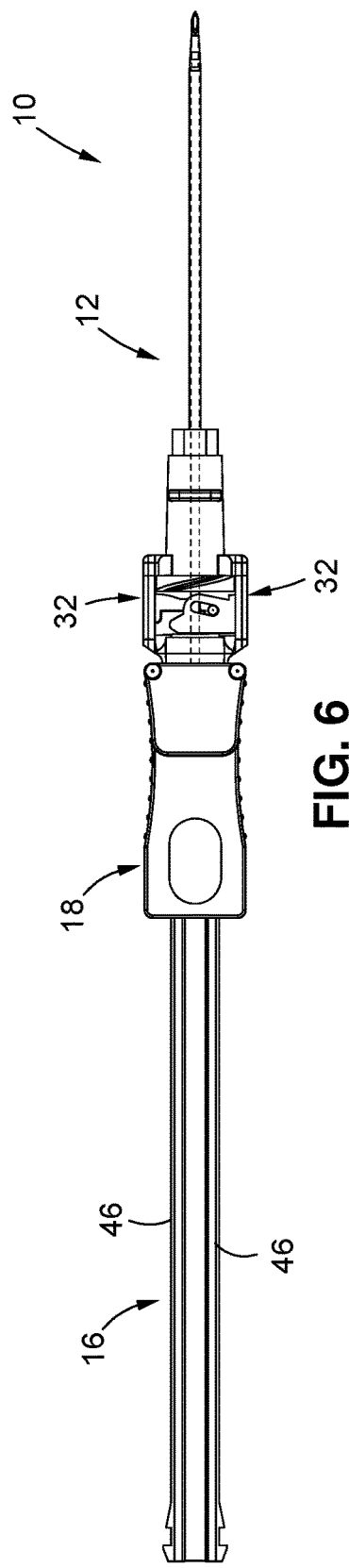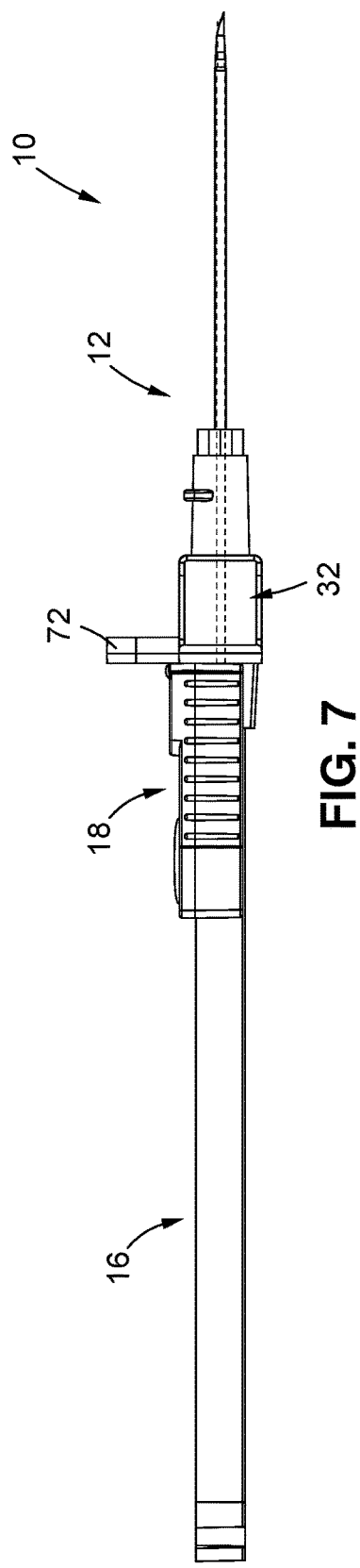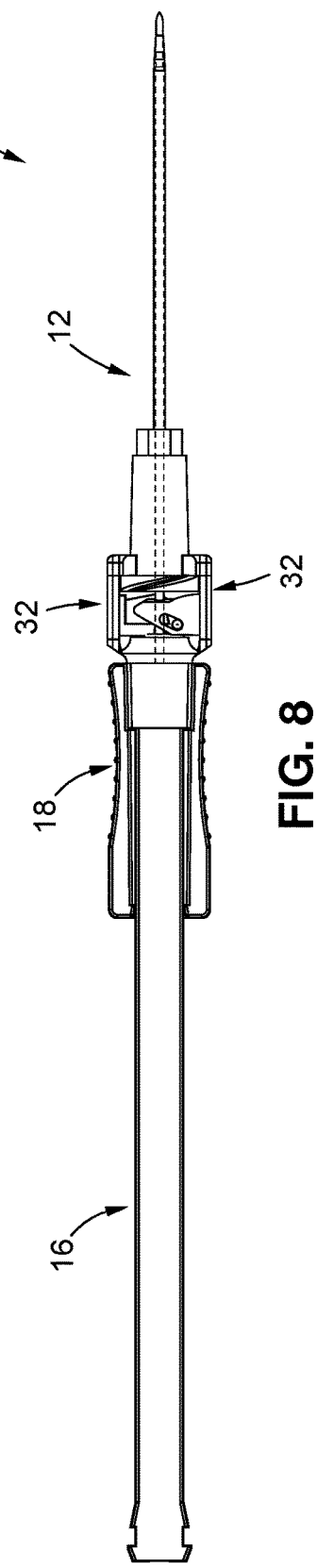

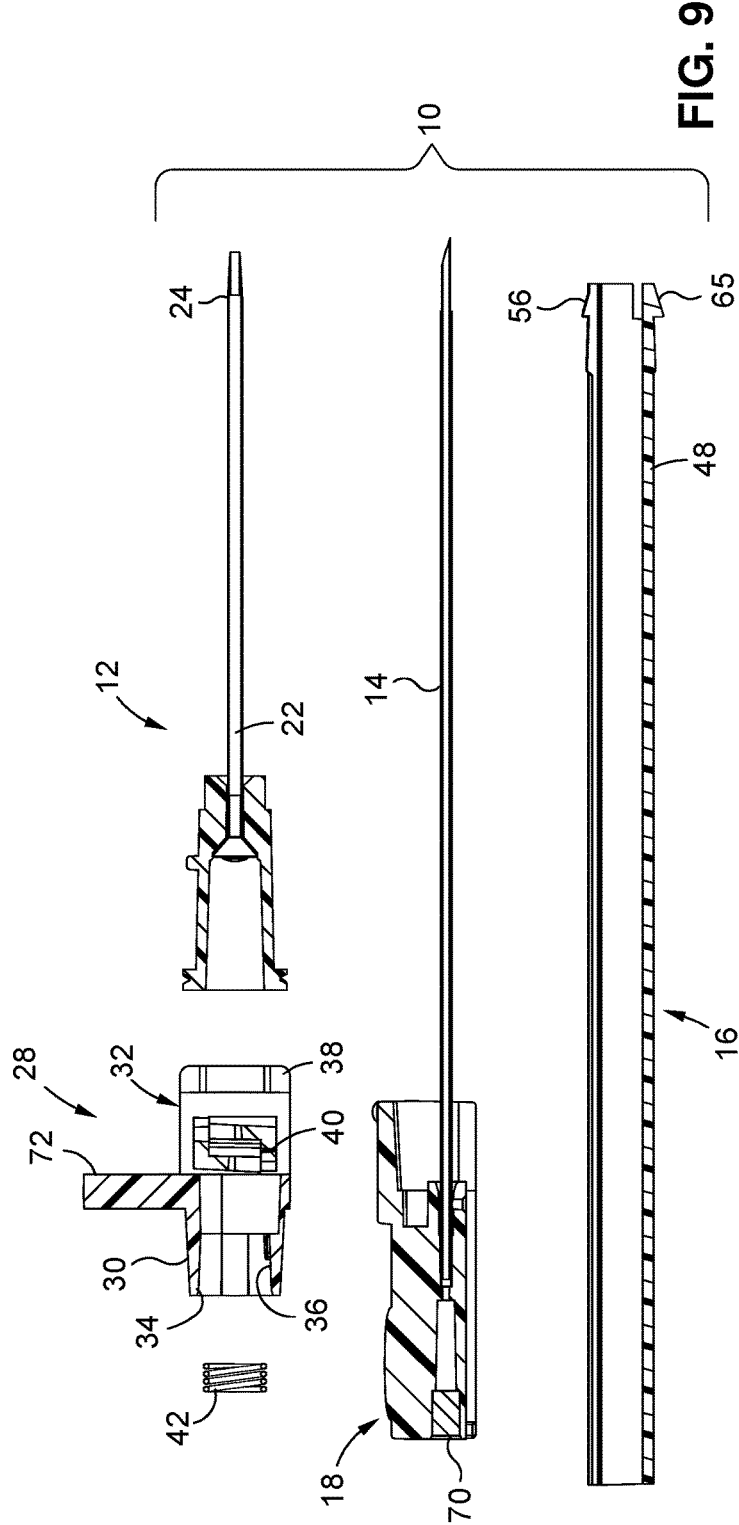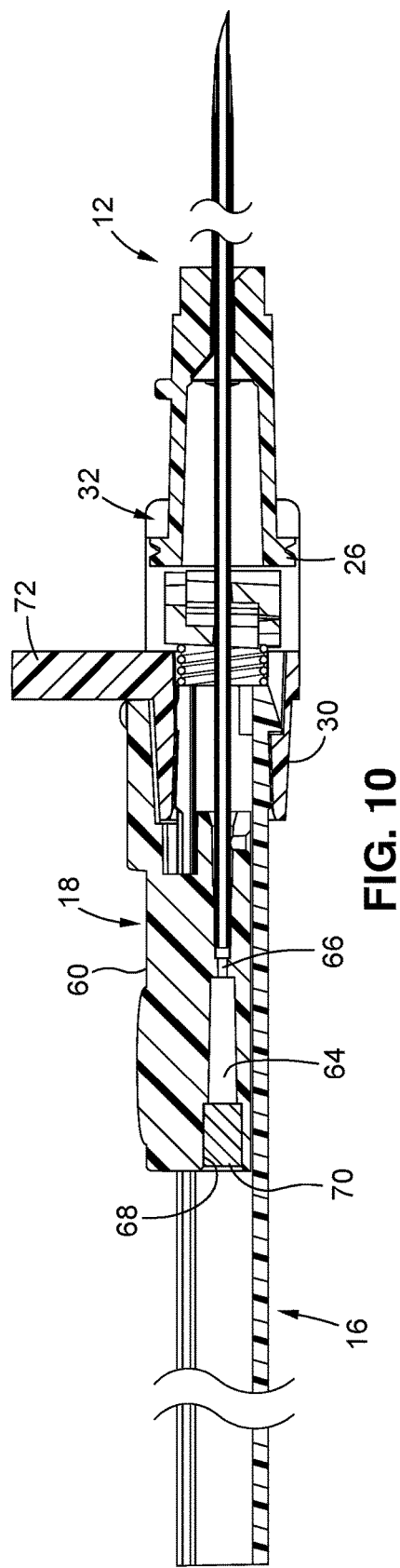

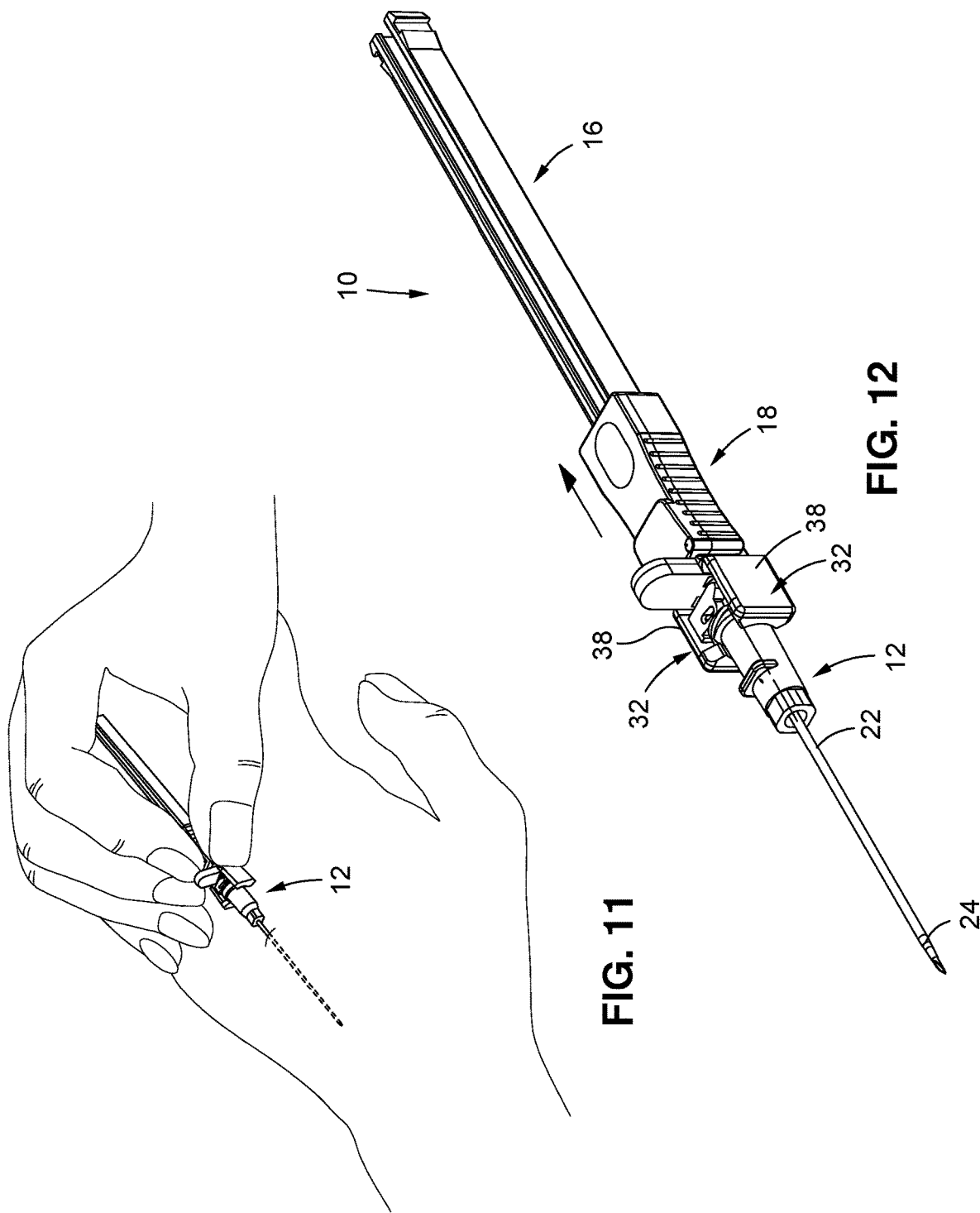

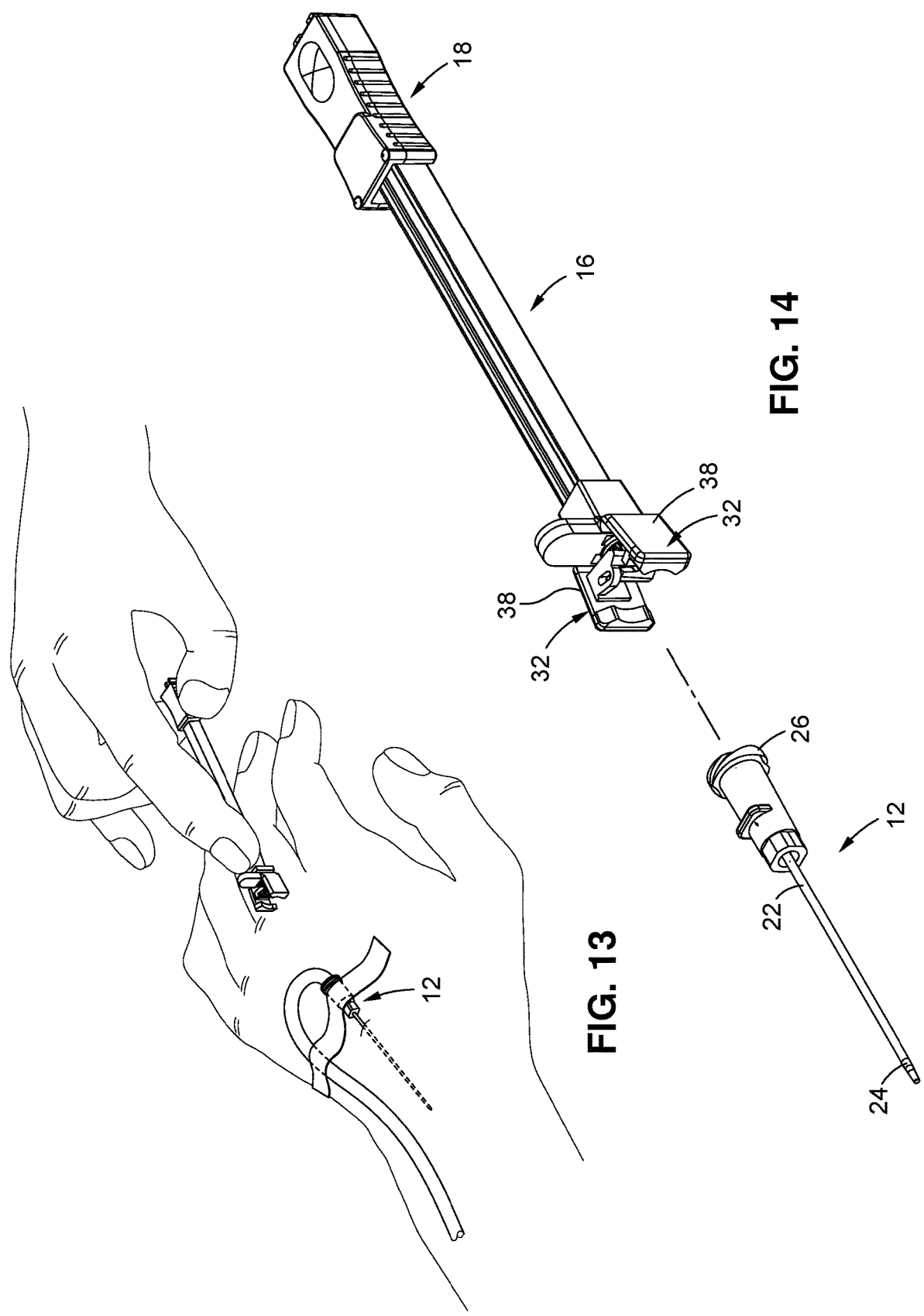

LOW PROFILE PASSIVE PROTECTOR FOR AN I.V. CATHETER

CROSS-REFERENCE TO RELATED APPLICATIONS

This application claims the benefit of U.S. Provisional Application No. 63/140,357 filed Jan. 22, 2021, the contents of which are expressly incorporated herein by reference.

STATEMENT RE: FEDERALLY SPONSORED RESEARCH/DEVELOPMENT

Not Applicable

BACKGROUND

1. Technical Field

The present disclosure relates generally to a universal passive protector for an IV catheter, and more specifically to a universal passive protector being specifically configured and adapted to allow for quick and easily assembly thereof.

2. Related Art

It is well known in the medical profession that various medical treatments and procedures oftentimes require the insertion or withdrawal of fluid from a patient. Intravenous needles are commonly employed to achieve such insertion or withdrawal of fluid. However, in some instances, the needle may be required to remain in the patient for an extended period of time, such as when introducing or withdrawing large amounts of fluid. Under these circumstances, metal needles are typically unfavorable due to their rigid structure and sharp distal tip which can cause trauma to the patient's vein. In view of the disadvantages associated with metal needles, medical professionals commonly use a catheter for such applications.

A conventional catheter typically includes a generally flexible tube having a hard/rigid distal tip. The catheter is typically inserted into a patient's vein using a catheter introduction device. Various catheter introduction devices have been developed and include through-the-needle catheters, as well as over-the-needle catheters. A through-the-needle catheter is inserted into an anatomical passage of the patient through the use of a cannula, which typically includes an elongate, metal needle which punctures the skin, tissue and vein wall to provide a path for placement of the catheter in the vein. When the needle pierces the vein, blood will "flashback" through the needle and into a flashback chamber typically located at the proximal end of the needle. Thus, the "flashback" is an indication to the medical technician that the needle has been properly inserted into the vein. At this point, the catheter is maintained stationary within the vein and the needle is withdrawn and removed from the catheter. The needle may have score lines formed therein to allow a medical technician to tear or pull the needle apart to remove the needle from the catheter once the catheter is removed from the patient.

Over-the-needle catheters are also commonly used by medical technicians, and typically include a thin catheter having a hub attached to its proximal end. The catheter is advanced over a rigid cannula, such as a needle, with the cannula and catheter being simultaneously advanced into a desired anatomical passage of a patient. Once the catheter has been inserted into the anatomical passage of the patient, the cannula is typically removed from the catheter by retracting the cannula through the catheter. The action of retracting the cannula can undesirably expose the medical technician as well as the patient to accidental contact with the cannula, particularly the piercing tip of the needle. Such accidental needle sticks are a serious concern in view of such diseases as Acquired Immune Deficiency Syndrome ("AIDS"), which can be transmitted through the exchange of bodily fluids with an infected person. In particular, a needle that has been used to place a catheter in the vein of an AIDS infected person may be a vehicle for transmission of the disease to the medical technician.

A number of protective devices have been developed recently to help reduce the incidence of disease and transmission through needle sticks. Many of the protective devices employ a protective, elongate sheath into which the needle is retracted as the needle is withdrawn from the patient. Along these lines, when the needle is withdrawn, its sharp distal tip is safely enclosed within the sheath, which is typically formed from a rigid material.

Operation of the protective devices generally includes an actuation mechanism connected to the needle, which is operated by the fingers of the medical technician. The technician uses various structures on the protective device to push against or pull on for retracting the needle within the sheath. However, in many protective devices, the flashback chamber is positioned in a manner which makes it difficult for the medical technician to easily grasp and manipulate the protective device in its intended manner. Such difficulty may lead to improper operation of the protective device, which may lengthen the process of inserting the catheter, or compromise the protective nature of the device.

Another deficiency associated with conventional protective devices pertains to the manufacture and assembly thereof. Conventional protective devices may include several components that require tedious and time-consuming assembly. As such, the cost and time associated with assembling conventional protective devices may be significant.

Accordingly, there is a need in the medical field for an improved protective device that is easy to assemble, and once assembled, is safe and easy to use. The present disclosure addresses this need, as will be discussed in more detail below.

BRIEF SUMMARY

According to an aspect of the disclosure, there is provided a low-profile universal passive protector for an IV catheter. The protector includes a connector having a tubular body and a pair of arms each being pivotally connected to the tubular body. The tubular body defines an end face, and the connector includes a cavity extending from the end face to the pair of arms. An elongate sheath defines a longitudinal axis, and the elongate sheath is snap engageable to the tubular body. A spring is insertable within the cavity of the connector and is configured to extend between at least one of the pair of arms and the elongate sheath when received within the cavity. A slider is moveably coupled to the sheath. The slider includes a flashback chamber formed therein. A hypodermic needle is connected to the slider and is in fluid communication with the flashback chamber. The slider is moveable along the sheath between a first position and a second position, with the hypodermic needle being drawn into the sheath as the slider moves from the first position toward the second position.

The slider may include a vent opening in fluid communication with the flashback chamber. The protector may additionally include a plug in the vent opening. The plug may be configured to restrict flow of liquid therethrough and to allow gas to pass therethrough.

The slider may include a transparent section in alignment with the flashback chamber to allow a user to view into the flashback chamber through the transparent section. The slider may be formed as a single integral body.

The protector may additionally include an over-the-needle catheter removeably disposed on the hypodermic needle. The over-the-needle catheter may include a hub and a tube connected to the hub, with the pair of arms being pivotable from an open position to a closed position to capture the hub within the pair of arms.

The connector may include a finger-press plate connected to the tubular body. The finger-press plate may extend beyond the slider in a direction perpendicular to the longitudinal axis to define a plate height when the slider is engaged with the elongate sheath and the elongate sheath is engaged with the tubular body.

Each of the pair of arms may include an opening formed therein. The hypodermic needle may be configured to pass through the openings of the pair of arms when the slider is in the first position. The hypodermic needle may be removed from the openings of the pair of arms when the slider is in the second position.

According to another embodiment, there is provided a method of assembling a low-profile universal passive protector for an IV catheter. The method includes inserting a spring into a connector having a tubular body and a pair of arms each being pivotally connected to the tubular body, with the spring being inserted into the tubular body of the connector. The method further includes positioning a sliding assembly in alignment with the connector. The sliding assembly including a slider and a hypodermic needle connected to the slider. The slider includes a flashback chamber therein, and the hypodermic needle is in fluid communication with the flashback chamber. The method also includes connecting an elongate sheath to the sliding assembling and the tubular body. The slider is slidably coupled to the sheath, and the sheath is connected to the connector via snap engagement.

The spring may be compressed in response to the elongate sheath being connected to connector. Compression of the spring may result in a force being imparted on the pair of arms to bias the pair of arms toward an open position.

The method may also include the step of connecting an over the needle catheter to the pair of arms.

The sliding assembly may be positioned relative to the connector such that the needle passes through both of the pair of arms.

The sliding assembly may be positioned relative to the connector such that the needle passes through the spring.

The flashback chamber may include an opening, and the step of connecting the sliding assembly to the sheath may include connecting the slider such that the opening to flashback chamber is positioned in a cavity formed in the sheath.

The sheath may be connected to the connector such that at least a portion of the sheath is received within the tubular body.

According to another embodiment, there is provided the method of assembling a low-profile universal passive protector for an IV catheter includes inserting a spring into a connector having a pair of pivoting arms. The method additionally includes positioning a sliding assembly adjacent the connector, with the sliding assembly including a slider and a hypodermic needle connected to the slider. The slider includes a flashback chamber therein, and the hypodermic needle is in fluid communication with the flashback chamber. The method further comprises connecting an elongate sheath to the connector and the sliding assembly. The elongate sheath is connected to the connector via snap engagement to compress the spring between the elongate sheath and at least one of the pair of pivoting arms. The elongate sheath is slidably connected to the sliding assembly.

The presently contemplated embodiments will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which:

FIG. 1 is an upper perspective view of a low-profile universal passive protector constructed in accordance with an embodiment of the present disclosure, the universal passive protector having a cover coupled thereto and extending over a hypodermic needle and an over-the-needle catheter;

FIG. 2 is an upper perspective view of the universal passive protector and cover, with the cover removed from the universal passive protector to expose the hypodermic needle and the over-the-needle catheter;

FIG. 6 is a top plan view of the universal passive protector;

FIG. 7 is a side view of the universal passive protector;

FIG. 8 is a bottom view of the universal passive protector;

FIG. 9 is an exploded side sectional view of the universal passive protector;

FIG. 10 is an assembled side sectional view of the universal passive protector;

FIG. 11 is an upper perspective view showing use of the universal passive protector for inserting a catheter into a patient;

FIG. 12 is an upper perspective view of the universal passive protector with the slider and needle in a deployed configuration;

FIG. 13 is an upper perspective view of the catheter detached from the sheath and inserted in a patient; and FIG. 14 is an upper perspective view of the catheter detached from the sheath and the hypodermic needle retracted within the sheath.

Common reference numerals are used throughout the drawings and the detailed description to indicate the same elements.

DETAILED DESCRIPTION

Figure 3:
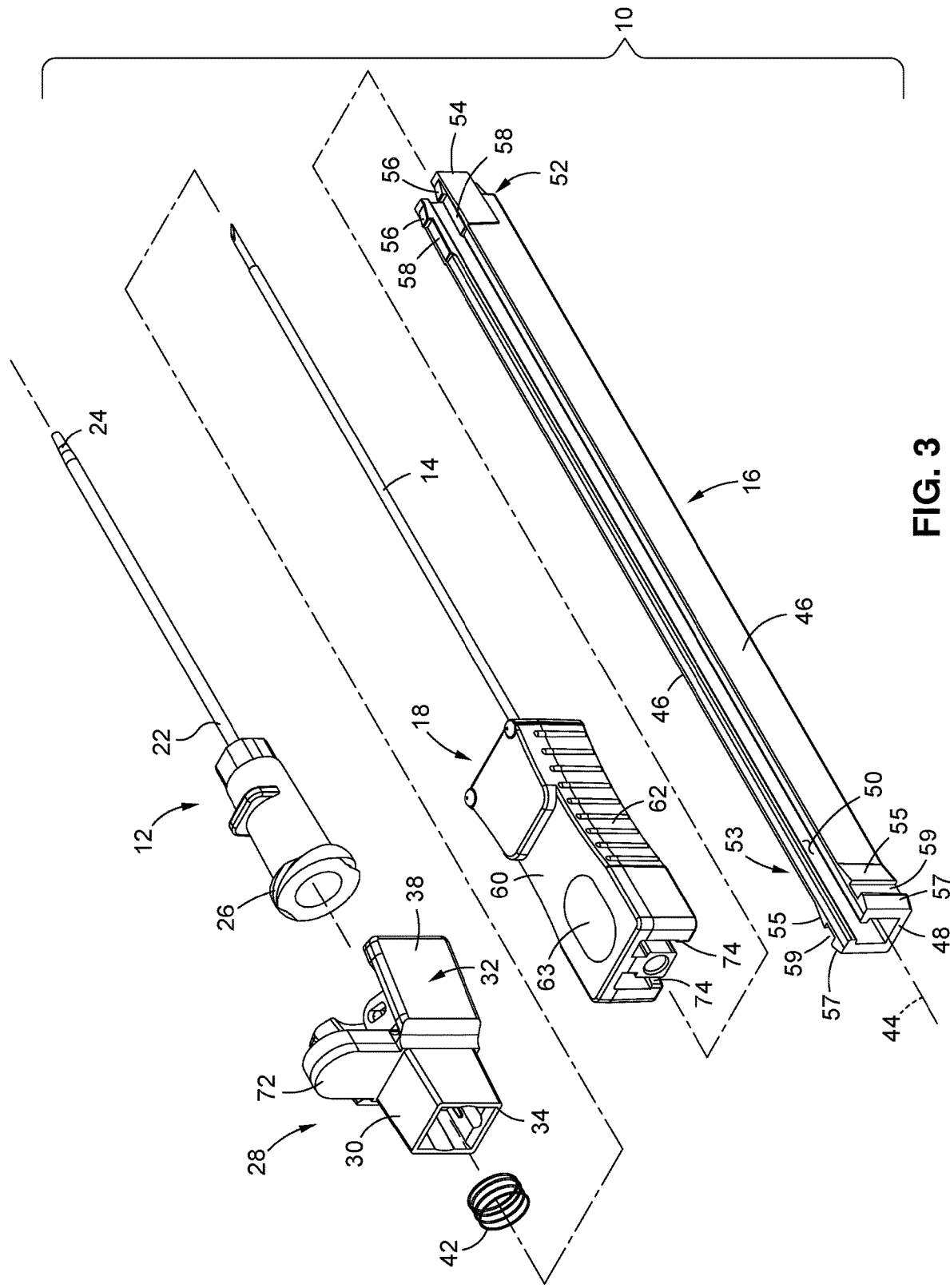
FIG. 3 is a rear, exploded, upper perspective view of the universal passive protector.
Figure 4:
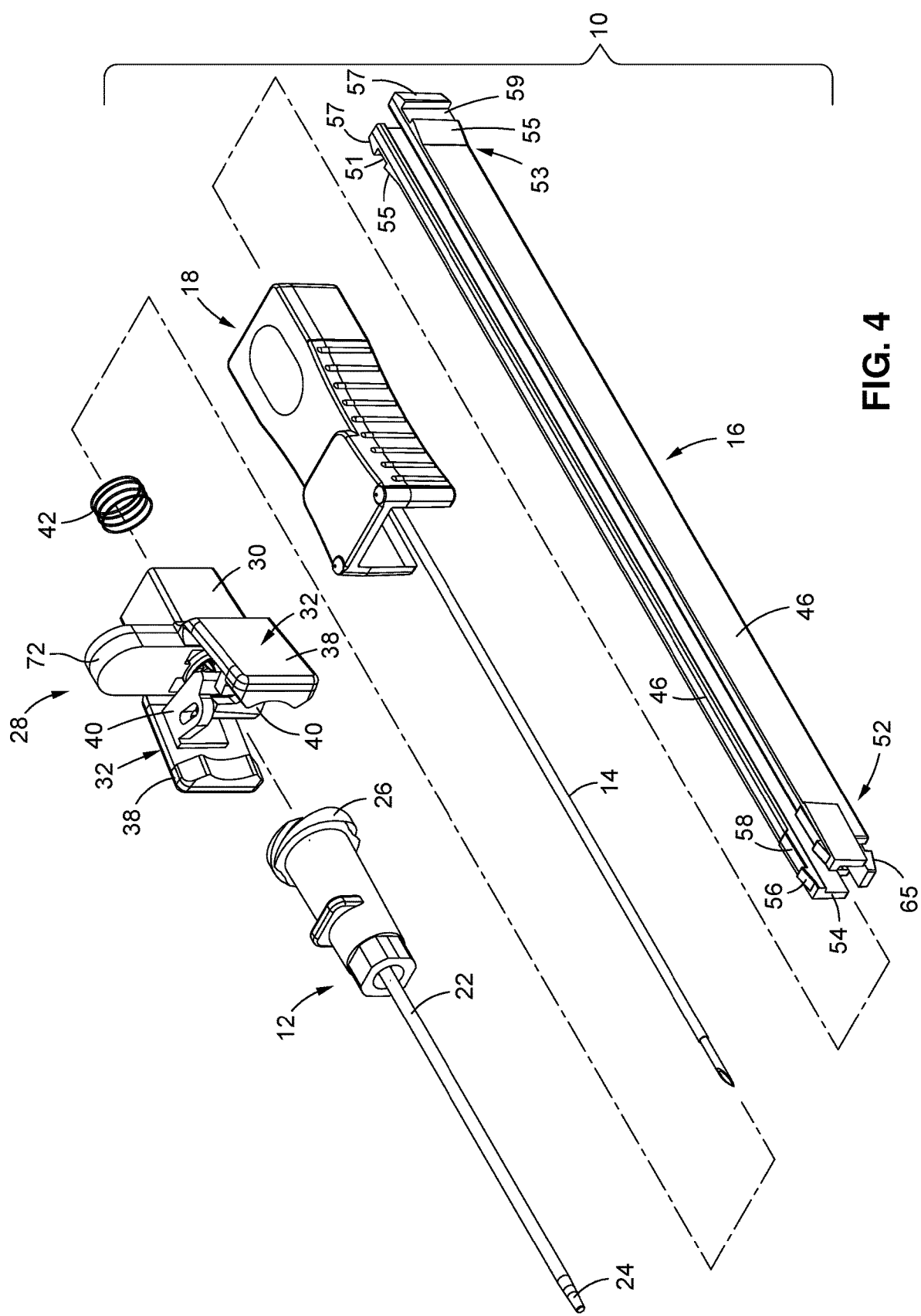
FIG. 4 is a front, exploded, upper perspective view of the universal passive protector.
Figure 5:
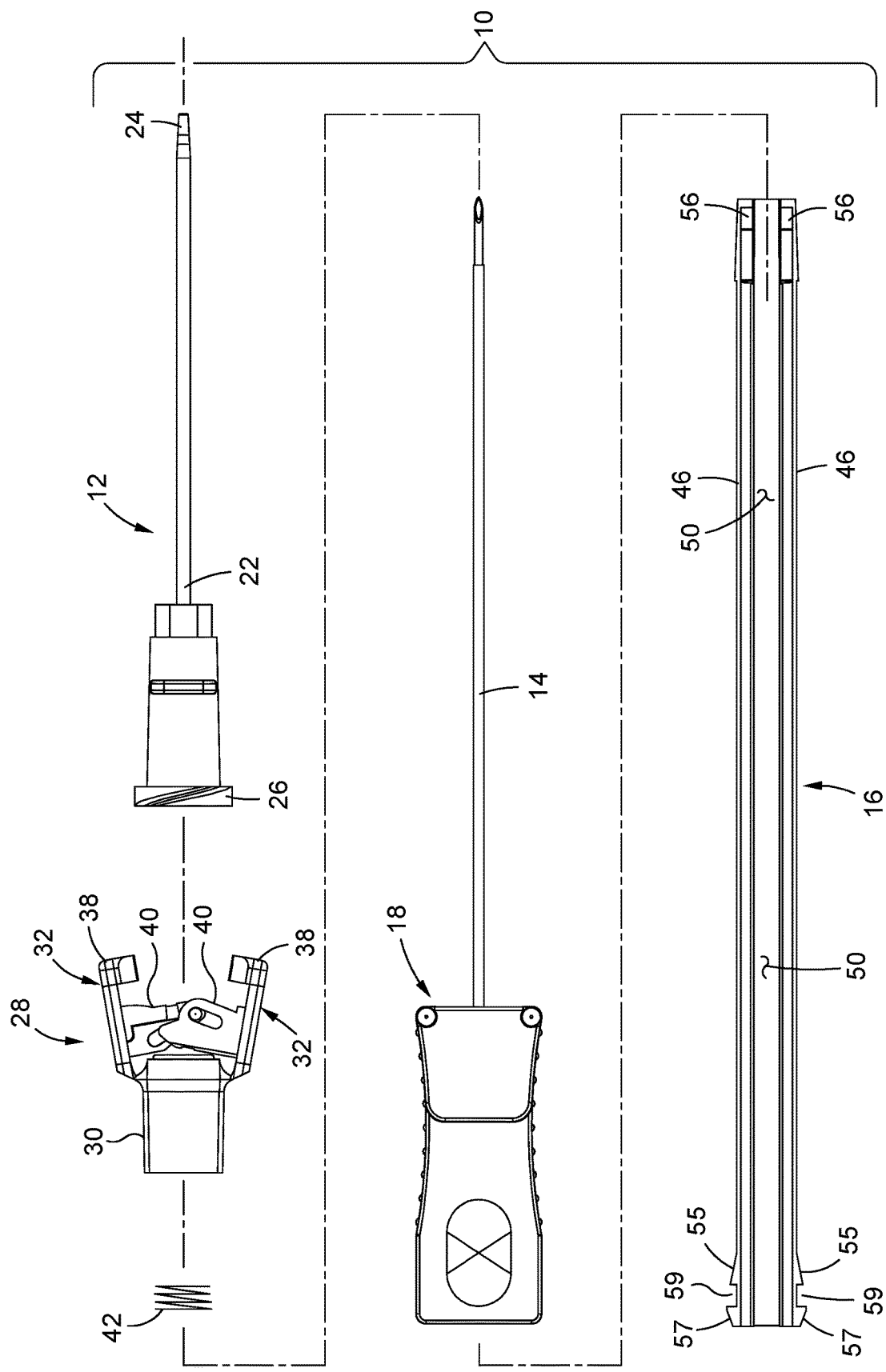
FIG. 5 is a top, exploded view of the universal passive protector.

The detailed description set forth below in connection with the appended drawings is intended as a description of the presently preferred embodiments of the disclosure, and is not intended to represent the only form in which the present devices may be developed or utilized. It is to be understood, however, that the same or equivalent functions may be accomplished by different embodiments that are also intended to be encompassed within the spirit and scope of the disclosure. It is further understood that the use of relational terms such as first, second, and the like are used solely to distinguish one from another entity without necessarily requiring or implying any actual such relationship or order between such entities.

Various aspects of the present disclosure are directed toward a low-profile passive protector 10 that may be specifically configured and adapted to allow for quick and easy assembly thereof. In particular, the various components of the protector 10 may be sized and configured to allow for snap-lock engagement therebetween. Furthermore, certain components of the protector 10 may be formed as a single integral unit to reduce the overall number of components, thereby reducing the number of steps that may be required to assemble the protector 10. Accordingly, the protector 10 may be assembled quicker and in a less costly manner than conventional passive protectors.

Referring now to FIGS. 1 and 2, there is shown a low-profile universal passive protector 10 for use in inserting an over-the-needle catheter 12 into a patient. The universal passive protector 10 includes a hypodermic needle 14 that is configured to be withdrawn into a sheath 16 in response to movement of a slider 18 along the sheath 16 from a deployed position to a retracted position. The universal passive protector 10 may include a detachable cover 20 that may be placed over the needle 14 and catheter 12 before using the protector 10 to protect a medical professional from an inadvertent needle stick. FIG. 1 shows the cover 20 extending over the needle 14 and catheter 12, while FIG. 2 shows the cover 20 as having been removed to expose the needle 14 and catheter 12.

The catheter 12 defines a proximal end portion 22, a distal end portion 24, and a catheter passageway extending between the proximal and distal end portions 22, 24. The catheter 12 includes a hub 26 positioned adjacent the proximal end portion 22. A catheter tube, formed of a soft, flexible material, is attached to the hub 26. The catheter tube is configured to be inserted into a patient's vein, thereby providing a path for intravenous injection or aspiration of the patient. Along these lines, the hub 26 is configured to be engageable with injection/aspiration devices via a threaded luer lock.

The protector 10 includes a connector 28 that is configured to engage with the catheter 12 on one end and with the sheath 16 on the other end. In particular, the connector 28 includes a tubular body 30 and a pair of arms 32 each being pivotally connected to the tubular body 30. The tubular body 30 includes an end face 34 and an inner surface 36 extending from the end face 34 to define a cavity extending into the tubular body 30 from the end face 34. The inner surface 36 may include a first region and a second region separated by an internal shoulder, which may be used to facilitate snap engagement with the sheath 16, as will be described in more detail below.

The tubular body 30 shown in the exemplary embodiment is quadrangular in configuration. In this regard, the word "tubular" as used herein refers to a structure having a wall that circumnavigates an opening, recess, or void. The word "tubular" does not refer to any specific shape or structure. Thus, the tubular body 30 may be other shapes (e.g., circular) in addition to being quadrangular.

The arms 32 are pivotally connected to the tubular body 30 and are moveable between a closed position and an open position. The arms 32 move closer together as they move from the open position toward the closed position, and away from each other as they move from the closed position toward the open position. According to one embodiment, each arm 32 includes a primary arm body 38 having a proximal segment coupled to the tubular body 30, and a distal segment configured to capture the hub 26 of the catheter 12 when the arms 32 are in the closed position. The arms 32 are connected to the tubular body 30 such that the primary arm bodies 38 are arranged in generally opposed relation to each other and define a hub receiving cavity therebetween. Each arm 32 additionally includes a secondary arm body 40 coupled to the primary arm body 38 and extending into the hub receiving cavity. According to one embodiment, one secondary arm body 40 includes a slot while the other secondary arm body includes a pin or post which resides within the slot to interlock the secondary arm bodies 40 to each other. The secondary arm bodies 40 may each include a central aperture, opening, slot, etc., formed therein to accommodate passage of the needle 14 therethrough. The central apertures are co-axially aligned with each other when the arms 32 are in the closed position, to thereby allow the needle 14 to extend through each aperture. When the needle 14 is captured within the sheath 16, and the arms 32 transition to the open position, the apertures move into a non-aligned configuration, which effectively prevents the needle 14 from leaving the sheath 16.

The foregoing describes an exemplary embodiment of the arms 32. A more detailed discussion of the arms 32 is presented in U.S. Pat. No. 6,981,965, entitled Universal Passive Protector for an IV Catheter, the content of which is expressly incorporated herein by reference.

The protector 10 additionally includes a spring 42 that is insertable into the tubular body cavity and is configured to bias the arms 32 toward the open position. The spring 42 may extend between the arms 32 and the sheath 16 when the sheath 16 is connected to the connector 28.

The tubular body 30 may be snap engageable with the sheath 16, which is an elongate member defining a longitudinal axis 44. The sheath 16 includes a pair of opposed side walls 46, a bottom wall 48, and a sheath cavity 50 extending into the sheath 16 from between the pair of side walls 46 along the length of the sheath 16. The sheath 16 may include a first end portion 52 configured to be snap engageable to the connector 28. In particular, the first end portion 52 may include a first end surface 54 and a pair of inclined surfaces 56. Each inclined surface 56 may extend from an upper surface 58 of a respective side wall 46. The end of each inclined surface 56 adjacent the first end surface 54 may be intersect the upper surface 58 of the side wall 46, while the opposite end of the inclined surface 56 may be spaced away from the upper surface 58 of the side wall to define a shoulder. The shoulders may be used to facilitate snap engagement with connector 28, as will be described in more detail below. The first end portion 52 may also include an inclined surface 65 extending from the bottom wall 48 to define a lower shoulder spaced from the first end surface 54. The lower shoulder may be additionally be used for facilitating snap engagement with the connector 28.

The sheath 16 may include a second end portion 53 opposite the first end portion 52, which is adapted to lock the slider 18 in response to the slider 18 being moved to a retracted position relative to the sheath 16. In particular, the sheath 16 may include a pair of locking tabs 55, each of which extends laterally outward from a respective side wall 46 of the sheath 16. Each locking tab 55 may include an inclined surface, which intersects the side wall 46 and then extends away from the side wall 46 in a direction from the first end portion of the sheath 16 to the second end portion 53 of the sheath 16. The sheath 16 may also include a pair of abutments 57 spaced from the locking tabs to define a stop groove 59 therebetween. A portion of the slider 18 may pass over the locking tabs and become captured in the stop groove 59 to lock the position of the slider 18 relative to the sheath 16.

The exemplary embodiment of the sheath 16 defines a substantially quadrangular cross section, although those skilled in the art will appreciate that the sheath 16 may define a variety of alternative cross-sectional shapes without departing from the spirit and scope of the present disclosure. For instance, the sheath 16 may also be round (e.g., circular).

The sheath 16 may be formed by injection molding or via other manufacturing techniques known in the art.

A slider 18 is slidably connected to the sheath 16 and is rigidly connected to the needle 14, such that movement of the slider 18 relative to the sheath 16 also results in movement of the needle 14 relative to the sheath 16. The slider 18 may be coupled to the sheath 16 and configured in a manner such that the slider 18 extends slightly above the upper surfaces 58 of the sheath 16 to and defines a slider upper surface 60. The slider 18 may also extend beyond the sides of the sheath 16 to define a pair of side surfaces 62. Each side surface 62 of the slider 18 may have a slight concave configuration and a plurality of ridges to enhance the ergonomic gripability of the slider 18. Along these lines, it is contemplated that a user will grip the slider 18 with the user's thumb and index finger being placed on respective side surfaces 62.

The slider 18 additionally includes a flashback chamber 64 formed therein and in fluid communication with the needle 14 to allow blood or other bodily fluid that passes through the needle 14 to flow into the flashback chamber 64. A portion of the slider upper surface 60 may include a transparent section 63 that is in alignment with the flashback chamber 64 to allow a user to view into the flashback chamber 64 through the transparent section. In one embodiment, the flashback chamber 64 is located in a lower portion of the slider 18 (e.g., below the upper surface 60) and is positioned within the sheath 16 cavity when the slider 18 is connected to the sheath 16. The slider 18 may also include a flashback inlet 66 connectable to the needle 14 and configured to form a fluid pathway between the needle 14 and the flashback chamber 64 when the needle 14 is connected to the flashback chamber 64. The slider 18 may further include a vent opening 68 in communication with the flashback chamber 64. A plug 70 is insertable within a vent opening 68 to prevent blood from exiting the flashback chamber 64. The plug 70 is preferably configured to allow gases to pass therethrough, while restricting the passage of liquids therethrough.

The slider 18 may also include a pair of locking tabs 74 configured to be received within a respective stop groove 59 on the sheath 16 when the slider 18 is in the retracted position. Each locking tab 74 may extend inwardly from a respective side wall of the slider 18.

According to one embodiment, the slider 18 is formed as a single, integral body. The slider 18 may be molded to form the unique contours and include the features (e.g., the flashback chamber 64, flashback inlet 66, and vent opening 68) discussed above. Forming the slider 18 as a single, integral unit may simply assembly of the protector 10.

The slider 18 is connectable to the sheath 16 such that the slider 18 is moveable along the length of the sheath 16 between a first, extended position and a second, retracted position. The slider 18 is rigidly connected to the needle 14 such that movement of the slider 18 from the extended position toward the retracted position causes the needle 14 to retract into the sheath 16 cavity. The slider 18 and sheath 16 may be cooperatively configured to lock the slider 18 in place when the slider 18 is moved into the retracted position so as to maintain the needle 14 within the sheath 16 for preventing inadvertent needle sticks.

The connector 28 may also include a finger-press plate 72, which may extend beyond the slider 18 to define a plate height when the slider 18 is engaged with the elongate sheath 16 and the elongate sheath 16 is engaged with the tubular body 30. The finger-press plate 72 may be specifically sized and configured to serve as a push-off point for the medical professional's index finger when transitioning the slider 18 from the extended position toward the retracted position.

The slider 18, which includes the flashback chamber 64, may be specifically sized and configured to define a low-profile relative to the finger-press plate 72 to allow the medical professional's index finger to easily interface with the finger-press plate 72. In this regard, the slider 18 may not interfere with the medical professional's index finger when the slider 18 is positioned adjacent the finger-press plate 72 (i.e., when the slider 18 is in the extended position). The slider 18 may be configured such that the slider 18 may be of a low-profile configuration, wherein the flashback chamber 64 does not extend above a finger-press plate 72 (e.g., no portion of the slider 18 may extend above the top of the finger-press plate 72—no portion of the slider 18 may traverse a transverse upper plane of the finger-press-plate 72). Thus, the flashback chamber 64 may not substantially impede the user's gripability of the protector 10 and operation thereof (e.g., movement of the slider 18 along the sheath 16).

With the basic structure of the components of the protector 10 described above, the following is a discussion of an exemplary method of assembling the protector 10.

The needle 14 may be connected to the slider 18 by attaching the needle 14 to the flashback inlet 66 to define a sliding assembly. The needle 14 may include an insertion end forming a sharp tip configured to be inserted into the patient, and an attachment end configured to be attached to the slider 18. An adhesive may be used to create a sufficient bond or interconnection between the needle 14 and the slider 18.

The over-the-needle catheter 12 may be connected to the connector 28 by inserting the hub 26 of the catheter 12 between the arms 32 when the arms 32 are in the open position. The arms 32 are then squeezed toward the closed position to capture the hub 26 therebetween. Squeezing the arms 32 to the closed position also results in the openings in the arms 32 to become aligned with each other.

The arms 32 may remain squeezed together to maintain engagement between the catheter 12 and the connector 28. The spring 42 may be inserted into the tubular body 30. The insertion end of the needle 14 may be inserted through the tubular body 30, through the spring 42, through the aligned openings in the arms 32, and through the over-the-needle catheter 12. Insertion of the needle 14 causes the slider 18 to move toward the connector 28. A front end of the slider 18 may extend over the tubular body 30 and may be disposed adjacent to or in abutment with the finger-press plate 72.

The sheath 16 may be connected to the slider 18 and the connector 28. In particular, the sheath 16 may be aligned relative to the slider 18 such that the flashback chamber 64 is positioned between the pair of side walls 46 of the sheath 16. The sheath 16 may be inserted in the slider 18, with the side walls 46 of the sheath 16 being received within respective channels formed in the slider 18 on opposite sides of the flashback chamber 64. The front end of the sheath 16 is further advanced into the tubular body 30 of the connector 28 until the shoulders on the sheath 16 pass over the shoulders in the tubular body 30, which effectuates snap engagement between the tubular body 30 and the sheath 16. In particular, once the shoulders of the sheath 16 are in abutment with the shoulders on the tubular body 30, the sheath 16 is restricted from being removed from the tubular body 30 in a direction opposite to insertion.

To insert the catheter 12 into the patient's vein using the protector 10, a medical professional grasps the protector 10 and aligns the distal, piercing end of the needle 14 with the patient's vein. The medical professional then punctures the patient's skin with the needle 14 and guides the needle 14 into the vein. When the needle 14 has penetrated the vein, the flashback chamber 64 fills with blood. The medical professional inserts the needle 14 into the vein deep enough so that the distal end of the catheter 12 traverses a wall of the vein.

When the catheter 12 has been safely inserted into the vein, the technician grasps the opposed sides of the slider between the professional's thumb and middle finger, while the technician's index finger resides on top of the slider 18 and against the finger-press plate. The low-profile configuration of the flashback body reduces interference with the professional's index finger when the slider 18 is in the extended position. In this regard, the professional has greater control over the device, which minimizes shaking of the needle 14 within the patient, and allows the user to more easily push/press against the finger-press plate for moving the slider.

The professional then pulls the slider 18 from the extended position toward the retracted position, which in turn, causes the needle 14 to retract into the sheath 16. When the slider 18 reaches the retracted position, the slider 18 may be locked in place on the sheath 16. Furthermore, when the needle 14 is completely retracted into the sheath 16, the arms 32 are no longer restrained by the needle 14, and thus spring into the open position. The catheter 12 is thus released from the arms 32 and is ready to engage with an injection or aspiration device. The needle 14 is safely stowed within the sheath 16 and the arms 32 block the needle 14 to prevent the needle 14 from exiting the sheath 16. In this regard, the protector 10 employs a redundant locking/needle capturing system including the engagement between the slider 18 and lock as well as the blockage of the needle 14 by the arms 32.

Additional information regarding use of the catheter is described in U.S. Pat. No. 8,956,328, entitled Low Profile Passive Protector For An I.V. Catheter, the content of which is expressly incorporated herein by reference.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show more details than is necessary for a fundamental understanding of the disclosure, the description taken with the drawings making apparent to those skilled in the art how the several forms of the presently disclosed disclosure may be embodied in practice.

What is claimed is:

1. A low-profile universal passive protector for an over-the-needle catheter comprising:
    a connector having a tubular body and a pair of arms each being pivotally connected to the tubular body, the tubular body defining an end face, the connector including a cavity extending from the end face to the pair of arms;
    an elongate sheath defining a longitudinal axis, the elongate sheath being snap engageable to the tubular body;
    a spring insertable within the cavity of the connector and configured to extend from at least one arm of the pair of arms to the elongate sheath when received within the cavity;
    a slider moveably coupled to the elongate sheath, the slider including a flashback chamber formed therein; and
    a hypodermic needle connected to the slider and in fluid communication with the flashback chamber;
    the slider being moveable along the elongate sheath between a first position and a second position, the hypodermic needle being drawn into the elongate sheath as the slider moves from the first position toward the second position.

2. The protector recited in claim 1, wherein the slider includes a vent opening in fluid communication with the flashback chamber.

3. The protector recited in claim 2, further comprising a plug in the vent opening, the plug being configured to restrict flow of liquid therethrough and to allow gas to pass therethrough.

4. The protector recited in claim 1, wherein the slider includes a transparent section in alignment with the flashback chamber to allow a user to view into the flashback chamber through the transparent section.

5. The protector recited in claim 1, wherein the slider is formed as a single integral body.

6. The protector recited in claim 1, further comprising the over-the-needle catheter removeably disposed on the hypodermic needle.

7. The protector recited in claim 6, wherein the over-the-needle catheter includes a hub and a tube connected to the hub, the pair of arms being pivotable from an open position to a closed position to capture the hub within the pair of arms.

8. The protector recited in claim 1, wherein the connector includes a finger-press plate connected to the tubular body, the finger-press plate extending beyond the slider in a direction perpendicular to the longitudinal axis to define a plate height when the slider is engaged with the elongate sheath, and the elongate sheath is engaged with the tubular body.

9. The protector recited in claim 1, wherein each of the pair of arms includes an opening formed therein, the hypodermic needle being configured to pass through the openings of the pair of arms when the slider is in the first position, and the hypodermic needle being removed from the openings of the pair of arms when the slider is in the second position.

10. A method of assembling a low-profile universal passive protector for an over-the-needle catheter, the method comprising the steps of:
    inserting a spring into a connector having a tubular body and a pair of arms each being pivotally connected to the tubular body, the spring being inserted into the tubular body of the connector;
    positioning a sliding assembly in alignment with the connector, the sliding assembly including a slider and a hypodermic needle connected to the slider, the slider including a flashback chamber therein, and the hypodermic needle being in fluid communication with the flashback chamber; and connecting an elongate sheath to the sliding assembly and the tubular body such that the spring extends from at least one arm of the pair of arms to the elongate sheath, the slider being slidably coupled to the elongate sheath, and the elongate sheath being connected to the connector via snap engagement.

11. The method recited in claim 10, wherein the spring is compressed in response to the elongate sheath being connected to the connector.

12. The method recited in claim 11, wherein compression of the spring results in a force being imparted on the pair of arms to bias the pair of arms toward an open position.

13. The method recited in claim 10, further comprising a step of connecting the over-the-needle catheter to the pair of arms.

14. The method recited in claim 10, wherein the sliding assembly is positioned relative to the connector such that the hypodermic needle passes through both of the pair of arms.

15. The method recited in claim 10, wherein the sliding assembly is positioned relative to the connector such that the hypodermic needle passes through the spring.

16. The method recited in claim 10, wherein the flashback chamber includes an opening, the step of connecting the sliding assembly to the elongate sheath includes connecting the slider such that the opening to the flashback chamber is positioned in a cavity formed in the elongate sheath.

17. The method recited in claim 10, wherein the elongate sheath is connected to the connector such that at least a portion of the elongate sheath is received within the tubular body.

18. A method of assembling a low-profile universal passive protector for an over-the-needle catheter, the method comprising the steps of:

inserting a spring into a connector having a pair of pivoting arms;

positioning a sliding assembly adjacent the connector, the sliding assembly including a slider and a hypodermic needle connected to the slider, the slider including a flashback chamber therein, and the hypodermic needle being in fluid communication with the flashback chamber; and connecting an elongate sheath to the connector and the sliding assembly, the elongate sheath being connected to the connector via snap engagement to compress the spring from the elongate sheath to at least one pivoting arm of the pair of pivoting arms, the elongate sheath being slidably connected to the sliding assembly.

19. The method recited in claim 18, wherein the flashback chamber includes an opening, the step of connecting the sliding assembly to the elongate sheath includes connecting the slider such that the opening to the flashback chamber is in a cavity formed in the elongate sheath.

20. The method recited in claim 18, wherein the elongate sheath is connected to the connector such that at least a portion of the elongate sheath is received within a tubular body of the connector.

* * * * *